(12) United States Patent
Schroecker et al.

(10) Patent No.: US 10,685,439 B2
(45) Date of Patent: Jun. 16, 2020

(54) IMAGING SYSTEM AND METHOD PROVIDING SCALABLE RESOLUTION IN MULTI-DIMENSIONAL IMAGE DATA

(71) Applicant: General Electric Company, Schenectady, NY (US)

(72) Inventors: Gerald Schroecker, Zipf (AT); Helmut Brandl, Zipf (AT); Erwin Fosodeder, Zipf (AT)

(73) Assignee: General Electric Company, Schenectady, NY (US)

( * ) Notice: Subject to any disclaimer, the term of this patent is extended or adjusted under 35 U.S.C. 154(b) by 134 days.

(21) Appl. No.: 16/019,875

(22) Filed: Jun. 27, 2018

(65) Prior Publication Data

US 2020/0005452 A1    Jan. 2, 2020

(51) Int. Cl.
| | |
|---|---|
| *G06K 9/00* | (2006.01) |
| *G06T 7/00* | (2017.01) |
| *A61B 8/08* | (2006.01) |
| *G06T 15/10* | (2011.01) |

(52) U.S. Cl.
CPC .......... *G06T 7/0012* (2013.01); *A61B 8/5207* (2013.01); *G06T 15/10* (2013.01); *G06T 2207/10076* (2013.01); *G06T 2207/10136* (2013.01); *G06T 2207/20028* (2013.01)

(58) Field of Classification Search
CPC .................. G06T 7/0012; G06T 15/10; G06T 2207/10076; G06T 2207/10136; G06T 2207/20028; A61B 8/5207
USPC ........................................ 382/128, 154, 131
See application file for complete search history.

(56) References Cited

U.S. PATENT DOCUMENTS

| | | | | |
|---|---|---|---|---|
| 5,785,889 A | * | 7/1998 | Greenfield | C09K 19/38 |
| | | | | 252/299.01 |
| 5,795,296 A | * | 8/1998 | Pathak | A61B 5/1075 |
| | | | | 600/443 |
| 6,530,885 B1 | * | 3/2003 | Entrekin | G01S 7/52053 |
| | | | | 128/916 |
| 7,601,121 B2 | | 10/2009 | Pagoulatos et al. | |
| 7,664,301 B2 | | 2/2010 | Kim et al. | |
| 8,280,483 B2 | * | 10/2012 | Zhu | G06F 19/321 |
| | | | | 600/407 |
| 8,976,934 B2 | | 3/2015 | Menianovich et al. | |
| 9,060,669 B1 | * | 6/2015 | Mo | A61B 8/565 |
| 9,918,700 B2 | | 3/2018 | El-Zehiry et al. | |
| 10,402,969 B2 | * | 9/2019 | Samset | G06T 7/0012 |
| 10,453,193 B2 | * | 10/2019 | Schroecker | A61B 8/5207 |
| 2001/0011969 A1 | | 8/2001 | Polz | |
| 2004/0126007 A1 | * | 7/2004 | Ziel | G06T 15/08 |
| | | | | 382/154 |

(Continued)

*Primary Examiner* — Marceau Milord
(74) *Attorney, Agent, or Firm* — The Small Patent Law Group LLC; Dean D. Small

(57) ABSTRACT

An imaging system and method acquire first ultrasound image data of a body at a first acquisition quality level, display one or more two-dimensional images of the body using the image data at the first acquisition quality level, and create second ultrasound image data at a reduced, second acquisition quality level. The second ultrasound image data is created from the first ultrasound image data that was acquired at the first acquisition quality level. The system and method also display a rendered multi-dimensional image of the body using the second ultrasound image data at the reduced, second acquisition quality level.

19 Claims, 7 Drawing Sheets

(56) References Cited

U.S. PATENT DOCUMENTS

| | | |
|---|---|---|
| 2006/0020207 A1 | 1/2006 | Jagoulatos et al. |
| 2006/0173326 A1* | 8/2006 | Thiele ................. A61B 8/06 600/440 |
| 2007/0167801 A1* | 7/2007 | Webler ................. G06T 19/00 600/459 |
| 2008/0208061 A1* | 8/2008 | Halmann ................. A61B 8/13 600/459 |
| 2009/0112095 A1* | 4/2009 | Daigle ................. A61B 8/06 600/454 |
| 2010/0286518 A1* | 11/2010 | Lee ................. A61B 8/4427 600/439 |
| 2010/0286519 A1* | 11/2010 | Lee ................. A61B 8/08 600/439 |
| 2011/0055148 A1* | 3/2011 | Berg ................. G06F 19/321 707/602 |
| 2011/0255762 A1* | 10/2011 | Deischinger .......... A61B 8/463 382/131 |
| 2012/0065499 A1* | 3/2012 | Chono ................. A61B 8/00 600/425 |
| 2012/0108960 A1* | 5/2012 | Halmann ............... A61B 8/461 600/437 |
| 2012/0116218 A1* | 5/2012 | Martin ................. A61B 8/4405 600/437 |
| 2012/0245465 A1* | 9/2012 | Hansegard ............. A61B 8/466 600/443 |
| 2013/0165785 A1* | 6/2013 | Lause ................. A61B 8/06 600/443 |
| 2013/0281854 A1* | 10/2013 | Stuebe ................. A61B 8/13 600/440 |
| 2014/0044325 A1* | 2/2014 | Ma ................. G06T 19/00 382/128 |
| 2014/0221832 A1 | 8/2014 | El-Zehiry et al. |
| 2014/0347388 A1* | 11/2014 | Friedman ................. A61B 8/08 345/629 |
| 2015/0141814 A1* | 5/2015 | Lee ................. A61B 6/5217 600/425 |
| 2015/0164330 A1* | 6/2015 | Perrey ................. A61B 5/0044 600/410 |
| 2015/0238168 A1 | 8/2015 | Poland |
| 2016/0015368 A1 | 1/2016 | Poland |
| 2016/0030008 A1* | 2/2016 | Gerard ................. A61B 8/5261 600/440 |
| 2016/0078623 A1 | 3/2016 | Forzoni et al. |
| 2016/0081658 A1* | 3/2016 | Perrey ................. A61B 8/5238 600/440 |
| 2016/0113632 A1 | 4/2016 | Ribes et al. |
| 2016/0144219 A1* | 5/2016 | Koenig ................. A63B 21/075 482/93 |
| 2016/0157828 A1* | 6/2016 | Sumi ................. G01S 15/8927 702/189 |
| 2016/0228091 A1* | 8/2016 | Chiang ................. G16H 30/20 |
| 2016/0328998 A1* | 11/2016 | Pedersen ................. G09B 23/28 |
| 2017/0209125 A1* | 7/2017 | Rai ................. G01B 11/14 |
| 2017/0238904 A1* | 8/2017 | Perrey ................. A61B 8/0883 |
| 2017/0238907 A1* | 8/2017 | Kommu Chs ......... A61B 8/483 |
| 2018/0085043 A1* | 3/2018 | Panicker ................. A61B 5/204 |
| 2018/0129782 A1* | 5/2018 | Himsl ................. G16H 30/20 |
| 2018/0206820 A1* | 7/2018 | Anand ................. A61B 8/4461 |
| 2019/0318484 A1* | 10/2019 | Dougherty ................. G06T 7/62 |
| 2019/0325620 A1* | 10/2019 | Adler ................. G06T 11/008 |
| 2019/0332900 A1* | 10/2019 | Sjolund ................. A61N 5/1039 |
| 2019/0350659 A1* | 11/2019 | Wang ................. A61B 8/0841 |
| 2019/0380685 A1* | 12/2019 | Schroecker .......... A61B 8/5207 |
| 2019/0388060 A1* | 12/2019 | Aase ................. A61B 8/463 |
| 2019/0392944 A1* | 12/2019 | Samset ................. G06T 7/0012 |

* cited by examiner

IMAGING SYSTEM AND METHOD PROVIDING SCALABLE RESOLUTION IN MULTI-DIMENSIONAL IMAGE DATA

FIELD

The subject matter disclosed herein relates generally to imaging systems.

BACKGROUND

Imaging systems generate image data representative of imaged bodies. Some types of imaging systems can generate multi-dimensional image data. For example, some ultrasound imaging systems can generate both two-dimensional image slices and three (or four) dimensional images or videos for viewing by operators of the imaging systems.

But, current imaging systems acquire the different dimensional types of images or videos at different resolutions because the image acquisition resolution used for one multi-dimensional image or video may not work for another, different multi-dimensional image or video. For example, lower resolution image data can provide for visually clearer and more appealing three-dimensional rendered images or four-dimensional rendered videos. But, this lower resolution image data may provide unclear or grainy two-dimensional image slices through the three-dimensional rendered images or four-dimensional videos. Conversely, higher resolution image data can provide for visually clearer and more appealing two-dimensional images. But, this higher resolution image data may provide unclear or bumpy three-dimensional rendered images or four-dimensional videos of the same imaged body.

To obtain both clear two-dimensional image slices and three- or four-dimensional rendered images or videos, current imaging processes may acquire image data of the same body twice. Once with a higher resolution (for better two-dimensional image slices) and another time with a lower resolution (for better three- or four-dimensional rendered images or videos). But, this additional imaging of the same body increases the time and workload needed to complete an imaging session with a person, and can limit how many imaging sessions can be completed within a day (or other time period).

BRIEF DESCRIPTION

In one embodiment, a method includes acquiring first ultrasound image data of a body at a first acquisition quality level, generating one or more two-dimensional images of the body using the image data at the first acquisition quality level, and creating second ultrasound image data at a reduced, second acquisition quality level. The second ultrasound image data is created from the first ultrasound image data that was acquired at the first acquisition quality level. The method also includes rendering a multi-dimensional image of the body using the second ultrasound image data at the reduced, second acquisition quality level. The multi-dimensional rendered image of the body can be a three dimensional image that is rendered or otherwise projected onto a two dimensional plane (e.g., an image plane). Alternatively, the multi-dimensional rendered image of the body can be a three dimensional image, such as an image that projects in at least three dimensions (e.g., along three orthogonal axes, but is stationary and not a video). This type of three dimensional image can be useful in examining or exploring in a virtual reality environment or the like. Optionally, the multi-dimensional rendered image of the body can be a fourth dimensional image, such as a video that projects in at least three dimensions (e.g., along three orthogonal axes) and that changes with respect to time (e.g., the fourth dimension in addition to the three axes). This type of four dimensional image can be useful in examining or exploring in a virtual reality environment or the like.

In one embodiment, a system includes one or more processors configured to receive first ultrasound image data of a body that was obtained at a first acquisition quality level. The one or more processors are configured to generate one or more two-dimensional images of the body using the ultrasound image data at the first acquisition quality level. The one or more processors also are configured to create second ultrasound image data at a reduced, second acquisition quality level from the first ultrasound image data that was acquired at the first acquisition quality level. The one or more processors also are configured to generate a multi-dimensional rendered image of the body using the second ultrasound image data at the reduced, second acquisition quality level.

In one embodiment, a method includes acquiring first ultrasound image data of a body at a first spatial resolution, generating two-dimensional image slices of the body using the ultrasound image data at the first spatial resolution, modifying the first ultrasound image data into second ultrasound image data by reducing the first spatial resolution of the first ultrasound image data to a second spatial resolution, and generating a three-dimensional rendered image of the body using the second ultrasound image data at the reduced, second spatial resolution.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
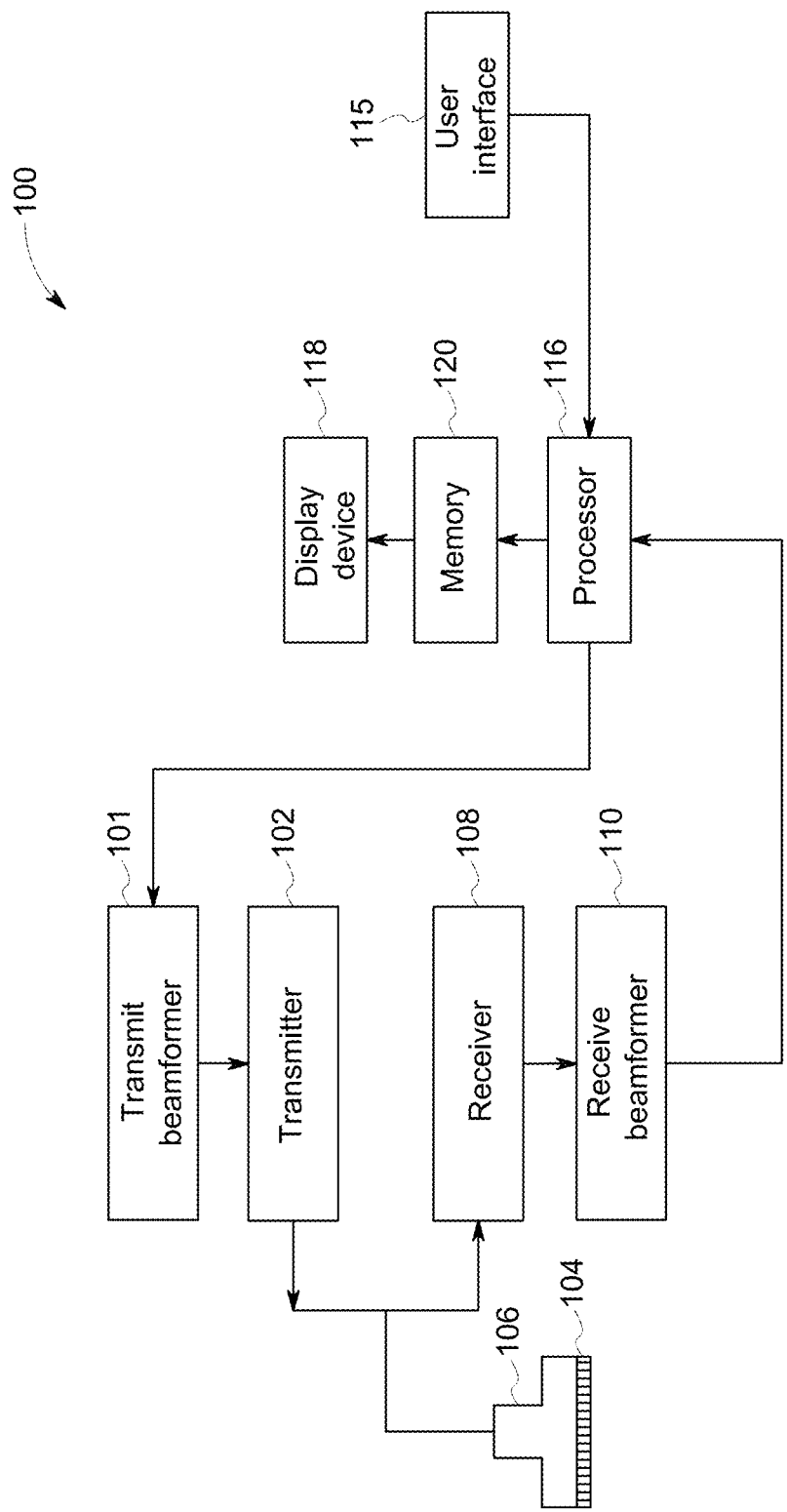
FIG. 1 is a schematic diagram of an ultrasound imaging system in accordance with one embodiment of the inventive subject matter described herein.

One or more embodiments of the inventive subject matter described herein provide imaging systems and methods that obtain image data of a body (e.g., a person or part of a person) at one or more different designated image quality levels, and then scale the image quality of the image data based on the type of multi-dimensional image or video that is rendered or otherwise formed from the image data. In one embodiment, the image qualities refer to different resolutions of the image data, but optionally can refer to another image quality, such as different magnifications, different line densities, different focal points or locations, different ultrasound frequencies, different colors, different brightness, or the like. As one example, the imaging system and method use the resolution(s) at which the image data was obtained to create lower multi-dimensional images (e.g., two-dimensional static images, which also can be referred to as image slices), but also can reduce the resolution of the image data to create higher multi-dimensional images (e.g., three-dimensional static rendered images or four-dimensional moving images, which also can be referred to as three-dimensional rendered videos). This allows for the imaging system to generate both higher resolution two-dimensional images and lower resolution rendered three- or four-dimensional images or videos from the same set of image data acquired during a single scan or imaging session of the body being imaged. The single scan of the body is performed by acquiring the image data at the same (e.g., higher) resolution, and the imaging system can use the image data at this higher resolution for some images while reducing the resolution to create other images or videos.

The multi-dimensional rendered images of the body that are described herein can be a three dimensional image that is rendered or otherwise projected onto a two dimensional plane (e.g., an image plane). Alternatively, the multi-dimensional rendered image of the body can be a three dimensional image, such as an image that projects in at least three dimensions (e.g., along three orthogonal axes, but is stationary and not a video). This type of three dimensional image can be useful in examining or exploring in a virtual reality environment or the like. Optionally, the multi-dimensional rendered image of the body can be a fourth dimensional image, such as a video that projects in at least three dimensions (e.g., along three orthogonal axes) and that changes with respect to time (e.g., the fourth dimension in addition to the three axes). This type of four dimensional image can be useful in examining or exploring in a virtual reality environment or the like.

At least one technical effect of the subject matter described herein provides an imaging system with the ability to generate clear images or videos of different dimensions (e.g., two-dimensional image slices and three- or four-dimensional rendered images or videos) using the same set of image data. The imaging system is able to scale or otherwise alter the resolution of the previously acquired image data to provide the different types of images or videos, while avoiding having to subject the body being imaged to multiple imaging scans at different resolutions.

FIG. 1 is a schematic diagram of an ultrasound imaging system 100 in accordance with one embodiment of the inventive subject matter described herein. The ultrasound imaging system 100 includes a transmit beamformer 101 and a transmitter 102 that drive elements 104 within a probe 106 to emit pulsed ultrasonic signals into a body (not shown). According to an embodiment, the probe 106 may be a two-dimensional matrix array probe. Another type of probe capable of acquiring four-dimensional ultrasound data may be used according to one or more other embodiments. The four-dimensional ultrasound data can include ultrasound data such as multiple three-dimensional volumes acquired over a period of time. The four-dimensional ultrasound data can include information showing how a three-dimensional volume changes over time.

The pulsed ultrasonic signals are back-scattered from structures in the body, such as blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. The probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. Scanning may include acquiring data through the process of transmitting and receiving ultrasonic signals. Data generated by the probe 106 can include one or more datasets acquired with an ultrasound imaging system. A user interface 115 may be used to control operation of the ultrasound imaging system 100, including, to control the input of person data, to change a scanning or display parameter, and the like.

The ultrasound imaging system 100 also includes one or more processors 116 that control the transmit beamformer 101, the transmitter 102, the receiver 108 and the receive beamformer 110. The processors 116 are in electronic communication with the probe 106 via one or more wired and/or wireless connections. The processors 116 may control the probe 106 to acquire data. The processors 116 control which of the elements 104 are active and the shape of a beam emitted from the probe 106. The processors 116 also are in electronic communication with a display device 118, and the processors 116 may process the data into images for display on the display device 118. The processors 116 may include one or more central processors (CPU) according to an embodiment. According to other embodiments, the processors 116 may include one or more other electronic components capable of carrying out processing functions, such as one or more digital signal processors, field-programmable gate arrays (FPGA), graphic boards, and/or integrated circuits. According to other embodiments, the processors 116 may include multiple electronic components capable of carrying out processing functions. For example, the processors 116 may include two or more electronic components selected from a list of electronic components including: one or more central processors, one or more digital signal processors, one or more field-programmable gate arrays, and/or one or more graphic boards. According to another embodiment, the processors 116 may also include a complex demodulator (not shown) that demodulates the radio frequency data and generates raw data. In another embodiment, the demodulation can be carried out earlier in the processing chain.

The processors 116 are adapted to perform one or more processing operations according to a plurality of selectable ultrasound modalities on the data. The data may be processed in real-time during a scanning session as the echo signals are received, such as by processing the data without any intentional delay or processing the data while additional data is being acquired during the same imaging session of the same person. For example, an embodiment may acquire images at a real-time rate of seven to twenty volumes per second. The real-time volume-rate may be dependent on the length of time needed to acquire each volume of data for display, however. Accordingly, when acquiring a relatively large volume of data, the real-time volume-rate may be slower. Some embodiments may have real-time volume-rates that are considerably faster than twenty volumes per second while other embodiments may have real-time volume-rates slower than seven volumes per second.

The data may be stored temporarily in a buffer (not shown) during a scanning session and processed in less than real-time in a live or off-line operation. Some embodiments of the inventive subject matter may include multiple processors (not shown) to handle the processing tasks that are handled by the processors 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, ten to thirty hertz. Images generated from the data may be refreshed at a similar frame-rate. Other embodiments may acquire and display data at different rates. For example, some embodiments may acquire data at a volume-rate of less than ten hertz or greater than thirty hertz depending on the size of the volume and the intended application.

A memory 120 is included for storing processed volumes of acquired data. In one embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium, such as one or more tangible and non-transitory computer-readable storage media (e.g., one or more computer hard drives, disk drives, universal serial bus drives, or the like).

Optionally, one or more embodiments of the inventive subject matter described herein may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters.

In various embodiments of the present invention, data may be processed by other or different mode-related modules by the processors 116 (e.g., B-mode, Color Doppler, M-mode, Color M-mode, spectral Doppler, Elastography, TVI, strain, strain rate, and the like) to form two- or three-dimensional image data. For example, one or more modules may generate B-mode, color Doppler, M-mode, color M-mode, spectral Doppler, Elastography, TVI, strain, strain rate and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may read the image volumes from a memory and displays an image in real time while a procedure is being carried out on a person. A video processor module may store the images in an image memory, from which the images are read and displayed.

The imaging system 100 exposes a body to ultrasound waves to obtain image data at a designated acquisition quality level. This quality level may define a resolution of the image data. The resolution of the image data indicates the degree of detail that is visible in an image or video formed by the image data. Higher resolutions indicate that more detail is visible in the image or video, so that smaller objects appear and are visible in the image or video. Lower resolutions indicate that less detail is visible in the image or video, so that some or all the smaller objects that appear in the higher resolution images or videos are not visible in the lower resolution images or videos. As one example, the resolution of image data can be the smallest spatial size of an object that is visible in the image or video formed from the image data.

Figure 2:
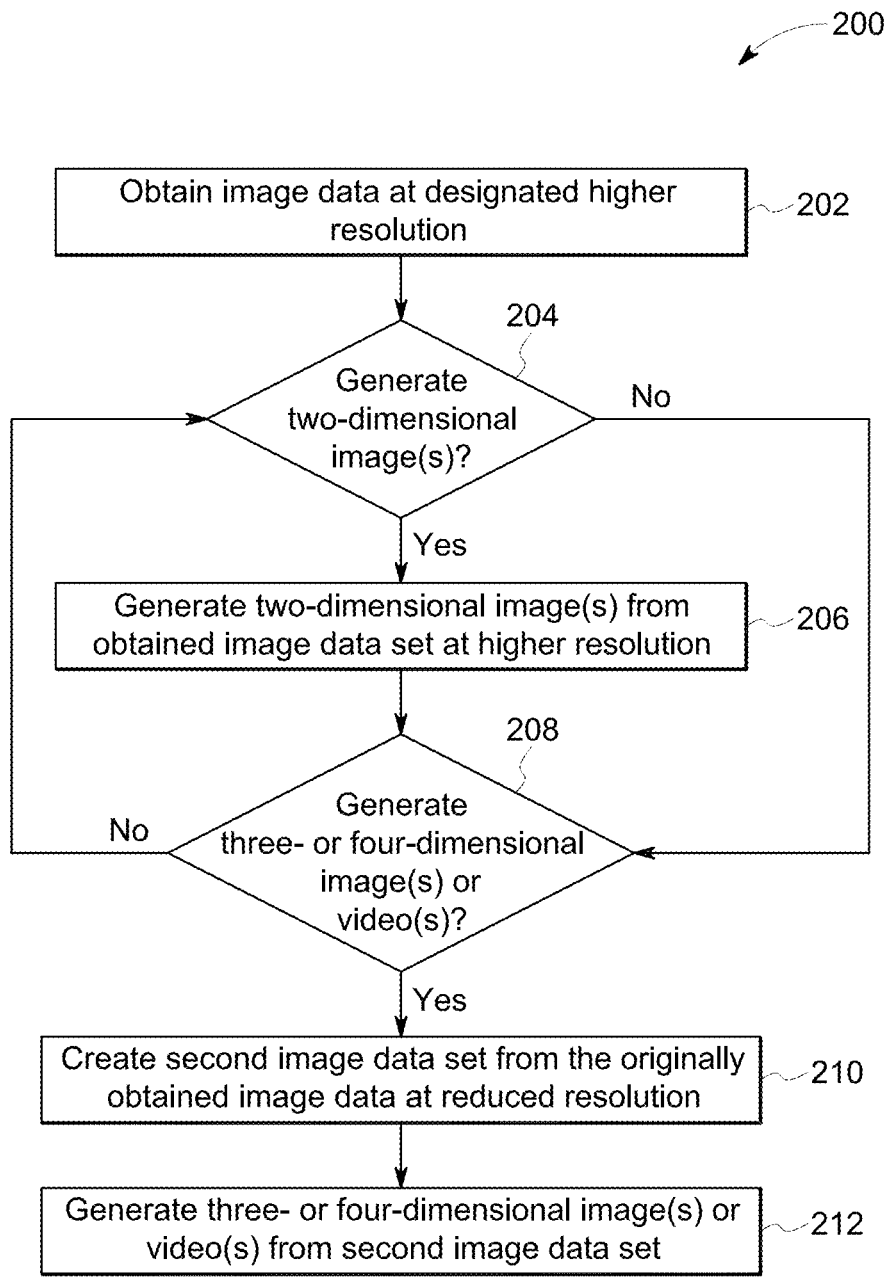
FIG. 2 illustrates a flowchart of one embodiment of a method for scaling the resolution of image data to generate different multi-dimensional images or videos.

FIG. 2 illustrates a flowchart of one embodiment of a method 200 for scaling the resolution of image data to generate different multi-dimensional images or videos. The method 200 can represent at least some operations performed by the processors 116 of the imaging system 100. At 202, image data of a body is acquired at a designated acquisition quality level. The acquisition quality level can define a resolution of the image data. This resolution can be referred to as a higher resolution as the image data is acquired at a resolution that optionally may be reduced to produce some types of images and/or videos, as described herein. As the resolution of the image data is increased, smaller and smaller objects become visible in the images and/or videos formed from the image data. But, noise in the image data also increases for higher resolutions.

Figure 3:
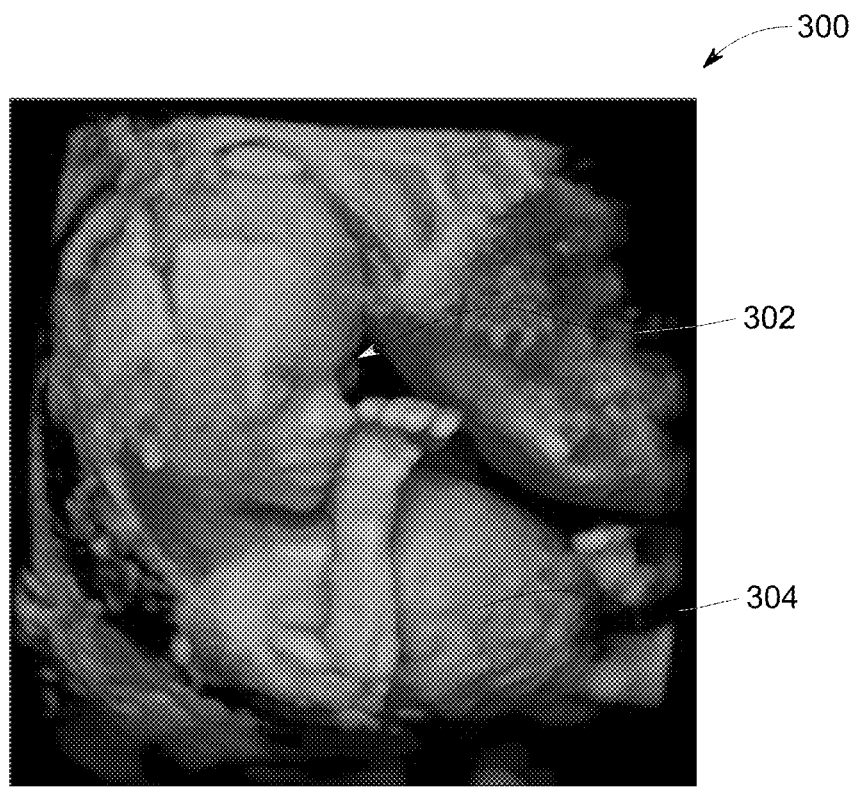
FIG. 3 illustrates an ultrasound image of a body that is generated from image data at a higher resolution.

For example, FIG. 3 illustrates an ultrasound image 300 of a body 302 that is generated from image data at a higher resolution. The image 300 can be a three-dimensional rendered image or a rendered frame of a four-dimensional video formed from higher resolution. The body 302 is a fetus, but alternatively may be another part of an anatomy or another body. As shown, the rendered image 300 includes several bumps 304, undulations, and the like, on various surfaces of the body 302. This is due to the higher resolution of the image data used to form the rendered image 300 revealing more and smaller objects or features of the body 302, and potentially due to the higher resolution image data having more electronic noise.

Figure 4:
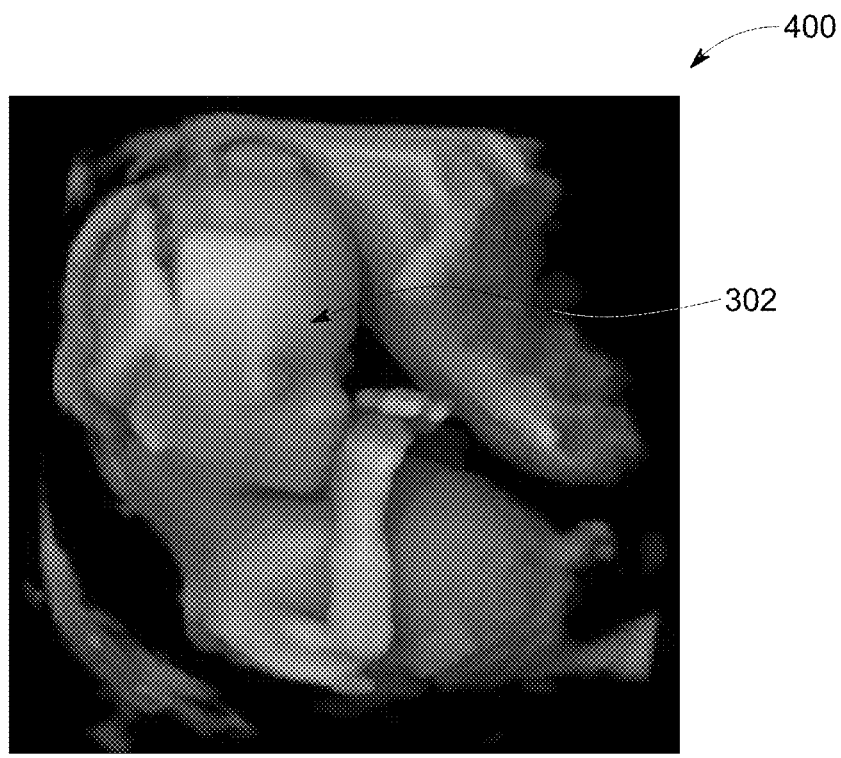
FIG. 4 illustrates another ultrasound image of the same body shown in FIG. 3 that is generated from image data at a lower resolution.

Conversely, FIG. 4 illustrates another ultrasound rendered image 400 of the same body 302 that is generated from image data at a lower resolution. The rendered image 400 can be a three-dimensional rendered image or a rendered frame of a four-dimensional video formed from image data at a lower resolution than the image data used to form the rendered image 300 in FIG. 3. In contrast to the rendered image 300 shown in FIG. 3, the rendered image 400 does not include as many bumps 304, undulations, and the like, on various surfaces of the body 302, or the bumps 304, undulations, and the like, do not appear as large in the rendered image 400 when compared with the rendered image 300. Instead, the surfaces of the body 302 appear smoother than the same surfaces of the same body 302 shown in FIG. 3. The surfaces of the body 302 appear smoother in FIG. 4 due to the lower resolution of the image data used to form the rendered image 400 revealing fewer objects or features of the body 302, and potentially due to the lower resolution image data having less electronic noise than the higher resolution image data.

Returning to the description of the flowchart of the method 200 shown in FIG. 2, at 204, a determination is made as to whether one or more two-dimensional images are to be generated from the image data obtained at the higher resolution. For example, the processors 116 can determine if an operator of the imaging system 100 has provided input via the user interface 115 that requests one or more two-dimensional image slices of the body 302 be formed. Alternatively, the processors 116 can automatically create the two-dimensional image slice(s) as a default action and without operator intervention. If one or more two-dimensional image slices are to be generated, then flow of the method 200 can proceed toward 206. But, if no two-dimensional image slices are to be generated, then flow of the method 200 can proceed toward 208.

Figure 5:
FIG. 5 illustrates a two-dimensional image slice that is generated using higher resolution image data.
Figure 6:
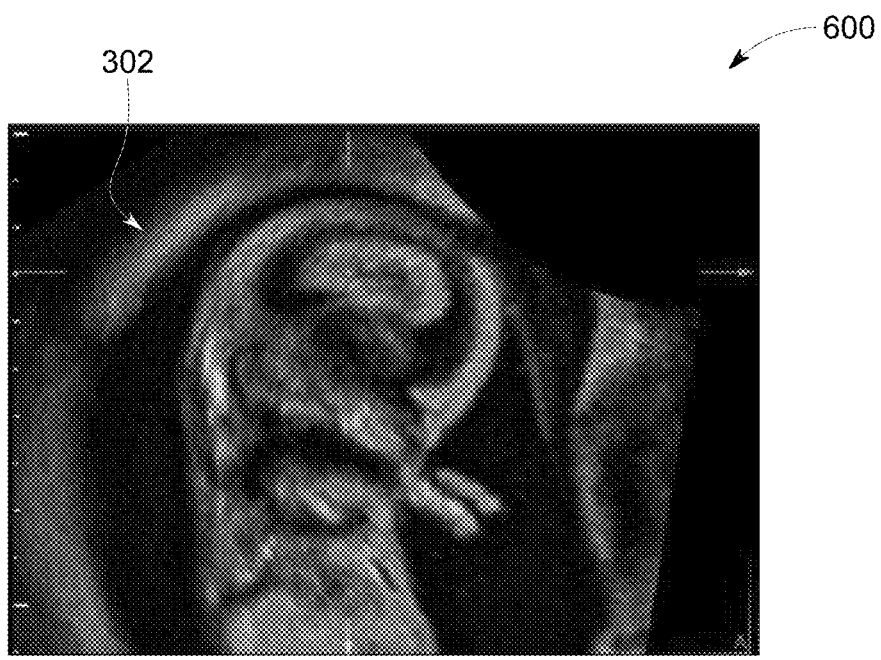
FIG. 6 illustrates a two-dimensional image slice of FIG. 5, but that is generated using lower resolution image data.
Figure 7:
FIG. 7 illustrates another two-dimensional image slice that is generated using higher resolution image data.
Figure 8:
FIG. 8 illustrates a two-dimensional image slice of FIG. 7, but that is generated using lower resolution image data.
Figure 9:
FIG. 9 illustrates another two-dimensional image slice that is generated using higher resolution image data.
Figure 10:
FIG. 10 illustrates the two-dimensional image slice of FIG. 9, but that is generated using lower resolution image data.

At 206, the two-dimensional images are generated. These images can be generated using the higher resolution image data obtained at 202. For example, the image slices can be created without reducing or otherwise modifying the resolution of the image data obtained at 202. FIGS. 5, 7, and 9 illustrate two-dimensional image slices 500, 700, 900 that are generated by the processors 116 using the image data obtained at the higher resolution. The image slices 500, 700, 900 represent images of planes extending through different portions of the imaged body 302. For example, the image slices 500, 700, 900 can be formed using the image data obtained at 202. FIGS. 6, 8, and 10 illustrate two-dimensional image slices 600, 800, 1000 that are generated by the processors 116 using the image data obtained at a lower resolution. The image slices 600, 800, 1000 represent images of planes extending through different portions of the imaged body 302. The image slices 500, 600 represent image slices of the same plane through the imaged body 302 but generated using different image data resolutions. The image slices 700, 800 represent image slices of the same plane through the imaged body 302 but generated using different image data resolutions. The image slices 900, 1000 represent image slices of the same plane through the imaged body 302 but generated using different image data resolutions. The image slices 500, 700, 900 are generated from greater image data resolution, while the image slices 600, 800, 1000 are generated from smaller image data resolution.

As shown in FIGS. 5 through 10, the image slices 500, 700, 900 provide sharper, clearer images of the body 302 than the image slices 600, 800, 1000. The edges, borders, lines, and the like, of imaged portions of the body 302 in the image slices 500, 700, 900 are more well-defined and clearer than the same edges, borders, lines, or the like, in the image slices 600, 800, 1000. This is due to the image data used to form the image slices 500, 700, 900 being at a higher resolution than the image data used to form the image slices 600, 800, 1000. Generating the image slices 500, 700, 900 using the higher resolution image data can provide clearer images to an operator of the imaging system 100, which can allow for the operator to more easily identify objects within the body 302. For example, more objects or features may be visible in the higher resolution image slices 500, 700, 900 than in the lower resolution image slices 600, 800, 1000. The image(s) that are created at 206 can be presented on the user interface 115 or on another display device by the processor 116.

Returning to the description of the flowchart of the method 200 shown in FIG. 2, at 208, a determination is made as to whether one or more three- or four-dimensional rendered images or videos are to be generated. For example, the processors 116 can determine if an operator of the imaging system 100 has provided input via the user interface 115 that requests one or more three- or four-dimensional rendered images or videos of the body 302 be formed. Alternatively, the processors 116 can automatically create the three- or four-dimensional rendered image or videos as a default action and without operator intervention. If one or more three- or four-dimensional rendered images or videos are to be generated, then flow of the method 200 can proceed toward 210. But, if no three- or four-dimensional rendered images or videos are to be generated, then flow of the method 200 can return toward 204. Alternatively, the method 200 can terminate or return to another operation.

At 210, a second image data set is created from the originally obtained image data set. The second image data set that is created can be the same image data obtained at 202, but with a smaller or lesser acquisition quality level. For example, the higher resolution of the image data obtained at 202 can be reduced to form the second image data set. The second image data set can be created by downsampling the original or first image data set. Downsampling the first image data set can involve reducing the amount of detail or information in the first image data set. For example, the second image data set can be created by calculating averages, medians, modes, or the like, of characteristic values of groups of voxels, pixels, etc., in the first image data set.

Figure 11:
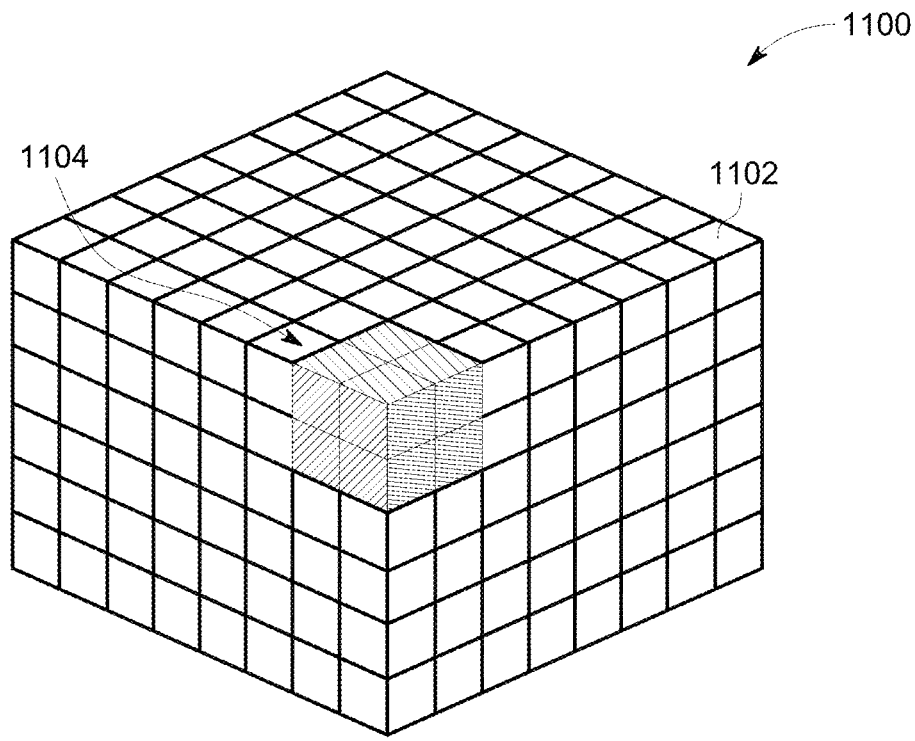
FIG. 11 schematically illustrates one example of a higher resolution image data set.

FIG. 11 schematically illustrates one example of a first image data set 1100. The first image data set 1100 can represent a portion of the image data that is obtained at 202 in the flowchart of the method 200 shown in FIG. 2. The first image data set 1100 is formed of several voxels 1102, which are three-dimensional volumes having characteristics that represent the body 302 that is imaged in a corresponding location. These characteristics can include intensities of the image data, colors of the body 302, etc. For example, a first voxel 1102 representing part of the body 302 may have a first color, while a second voxel 1102 representing space around the body 302 (but not including the body 302) may have a different, second color to indicate that the first voxel 1102 represents the body 302 and the second voxel 1102 does not represent the body 302. While the description of the higher and lower resolution image data sets focuses on voxels 1102 as forming different parts of each of the image data sets, alternatively, the different image data sets can be described as being formed from two-dimensional pixels or the like.

The second, reduced resolution image data set can be formed by calculating representative values of different groups 1104 of the voxels 1102 in the first image data set 1100, and using these values to represent the different groups 1104 of the voxels 1102. For example, a representative value can be calculated for each non-overlapping, mutually exclusive group 1104 of eight voxels 1102 in the first image data set 1100. These groups 1104 may be non-overlapping and mutually exclusive in that no two groups 1104 share or include the same voxel 1102. Alternatively, two or more of the groups 1104 of voxels 1102 may include the same voxel 1102. While the description herein focuses on calculating representative voxel values for groups 1104 of eight voxels 1102, alternatively, each group 1104 of voxels 1102 may include a different integer number of voxels 1102, such as nine voxels 1102, twenty-seven voxels 1102, etc. Alternatively, each group 1104 of voxels 1102 can include a non-integer number of voxels 1102, such as 3.5 voxels 1102, 6.5 voxels 1102, etc. The characteristic value for the non-integer group 1104 of voxels 1102 can be calculated by sharing voxels 1102 between two or more groups 1104 of voxels 1102.

Figure 12:
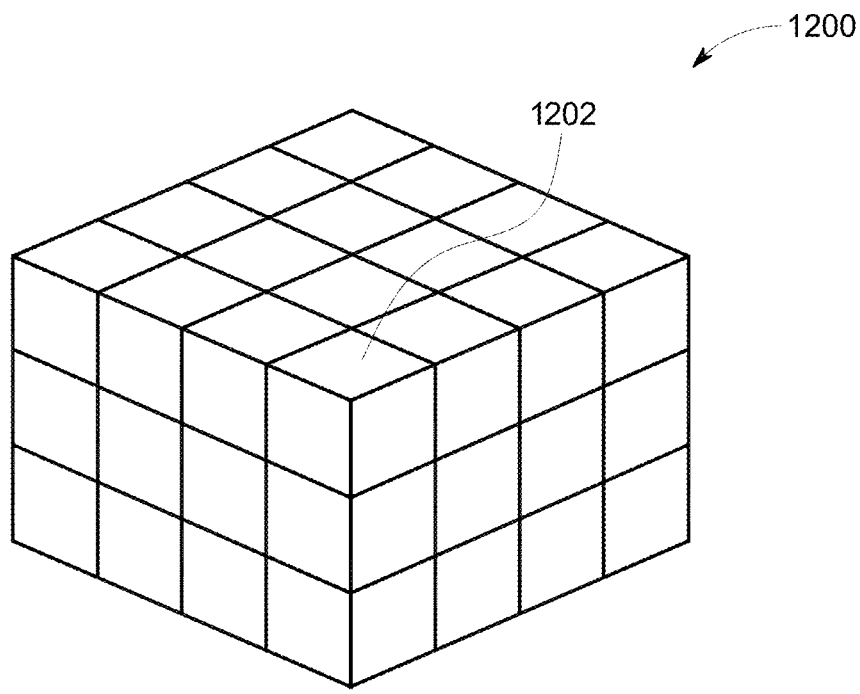
FIG. 12 schematically illustrates one example of a lower resolution image data set that is created from the image data set shown in FIG. 11.

FIG. 12 schematically illustrates one example of a second image data set 1200. The second image data set 1200 can represent a portion of the image data that is created obtained at 210 in the flowchart of the method 200 shown in FIG. 2. The second image data set 1200 is formed of a lesser number of voxels 1202 relative to the first image data set 1100. Individual voxels 1202 in the second image data set 1200 may be larger than individual voxels 1102 in the first image data set 1100. For example, each voxel 1202 may represent the average, median, mode, or the like, value of the characteristics of a group 1104 of voxels 1102 in the first image data set 1100. Alternatively, individual voxels 1202 in the second image data set 1200 may be the same size (or smaller) than the individual voxels 1102 in the first image data set 1100. For example, the average, median, mode, etc. value that is calculated from the voxels 1102 in a group 1104 in the first image data set 1100 may be assigned to each of the voxels 1202 in the same sized group of voxels 1202 in the second image data set 1200.

In the illustrated example, the voxel 1202 that is labeled in FIG. 12 can represent the average value of the intensities of the voxels 1102 in the group 1104 that is labeled in FIG. 11. For example, an average of the intensity values of the image data associated with the voxels 1102 shown in FIG. 11 in cross-hatching can be calculated. This average value can be assigned to the entire voxel 1202 that is labeled in FIG. 12. Values for other voxels 1202 in the second image data set 1200 can be calculated as average values for corresponding groups 1104 of other voxels 1102. As shown in FIGS. 11 and 12, downsampling the first image data set 1100 by calculating representative values of the voxels 1102 in different groups 1104 of voxels 1102 can reduce the amount of information in the second image data set 1200. This can reduce the resolution of the second image data set 1200 relative to the first image data set 1100.

Optionally, the second image data can be created from the first image data in another manner. As one example, the second image data can be created by sampling the first image data. The second image data can be formed by taking every $n^{th}$ sample of the first image data, where n is greater than one. This can be achieved by obtaining every second sample of the first image data to form the second image data (e.g., to reduce the resolution in half), every fourth sample of the first image data to form the second image data (e.g., to reduce the resolution by three-quarters), and the like. As another example, the second image data can be created by calculating an average of n samples, where n is greater than one. For example, the second image data can be formed from averages or medians of many of the samples of the first image data described above. In another example, the second image data can be formed by convoluting the first image data with a kernel filter, such as a lowpass filter kernel. A lowpass filter kernel can be applied to the first image data to form the second image data by averaging values of adjacent voxels or pixels in the first image data, by averaging values of groups of three or more neighboring voxels or pixels in the first image data, or the like. In another example, the second image data can be formed by applying one or more non-linear filters to the first image data, such as an anisotropic diffusion filter, another diffusion filter, a bilateral filter, etc.

Returning to the description of the flowchart of the method 200 shown in FIG. 2, at 212, a multi-dimensional video or rendered image is created from the reduced resolution image data set. For example, a three-dimensional rendered image or four-dimensional video can be created from the second data set that is downsampled from the image data set obtained at 202. Creating the three- or four-dimensional rendered image or video from the reduced resolution image data can provide a clearer or smoother image of the body 302. For example, the image data shown in FIG. 4 is created from a reduced resolution image data set (relative to the image data shown in FIG. 3). The reduced detail or information in the lower resolution image data set can reduce the presence of bumps, undulations, or other small objects in the rendered image or video (as shown by a comparison of the images shown in FIGS. 3 and 4). The rendered image(s) or video(s) that are created at 212 can be presented on the user interface 115 or on another display device by the processor 116.

Flow of the method 200 can then terminate, or can return to one or more prior operations. For example, flow of the method 200 can return toward 202 for the acquisition of additional image data.

In another embodiment, the method 200 can be used to create three-dimensional models for additive manufacturing instead of or in addition to creating multi-dimensional images or videos. For example, the higher resolution image data set obtained at 202 can be a scan or imaging of a three-dimensional object, such as a part of a machine. The image data set can be ultrasound image data, or can be image data from another type of imaging modality. This image data set may include too much detail such that creating a three-dimensional printed article from the image data set would include many undesirable bumps, undulations, and the like, and few smooth surfaces. Stated differently, the three-dimensional printed article may appear very different from the original machine part. The image data set can be downsampled to create a reduced resolution image data set at 210. This reduced resolution image data set can then be used as an input to an additive manufacturing system, such as a three-dimensional printing system. This reduced resolution image data set can be used by the manufacturing or printing system to create the three-dimensional printed article, which will have fewer bumps, undulations, and the like, and may have a shape and appearance that is closer to the original machine part (than the three-dimensional printed article formed from the higher resolution image data set).

In one embodiment, a method includes acquiring first ultrasound image data of a body at a first acquisition quality level, generating one or more two-dimensional images of the body using the image data at the first acquisition quality level, and creating second ultrasound image data at a reduced, second acquisition quality level. The second ultrasound image data is created from the first ultrasound image data that was acquired at the first acquisition quality level. The method also includes rendering a multi-dimensional image of the body using the second ultrasound image data at the reduced, second acquisition quality level.

Optionally, the first acquisition quality level is a first spatial resolution of the first ultrasound image data and the second acquisition quality level is a reduced, second spatial resolution of the first ultrasound image data.

Optionally, creating the second ultrasound image data includes averaging values of one or more of pixels or voxels in the first ultrasound image data.

Optionally, creating the second ultrasound image data includes reducing a spatial resolution of the first ultrasound image data.

Optionally, creating the second ultrasound image data includes applying a low-pass kernel filter to the first ultrasound image data.

Optionally, rendering the second ultrasound image data includes downsampling the first ultrasound image data.

Optionally, the second ultrasound image data is obtained without exposing the body to additional ultrasound pulses following acquisition of the first ultrasound image data.

Optionally, the multi-dimensional image of the body that is rendered is a three-dimensional image of the body.

Optionally, the one or more two-dimensional images represent two-dimensional slices through the body.

Optionally, the first ultrasound image data is three-dimensional ultrasound image data.

Optionally, the first ultrasound image data is four-dimensional ultrasound image data.

Optionally, the method also includes forming a three-dimensional object based on the second ultrasound image data.

In one embodiment, a system includes one or more processors configured to receive first ultrasound image data of a body that was obtained at a first acquisition quality level. The one or more processors are configured to generate one or more two-dimensional images of the body using the ultrasound image data at the first acquisition quality level. The one or more processors also are configured to create second ultrasound image data at a reduced, second acquisition quality level from the first ultrasound image data that was acquired at the first acquisition quality level. The one or more processors also are configured to render a multi-dimensional image of the body using the second ultrasound image data at the reduced, second acquisition quality level.

Optionally, the first acquisition quality level is a first spatial resolution of the first ultrasound image data and the second acquisition quality level is a reduced, second spatial resolution of the first ultrasound image data.

Optionally, the one or more processors are configured to create the second ultrasound image data by reducing a spatial resolution of the first ultrasound image data.

Optionally, the one or more processors are configured to create the second ultrasound image data by averaging values of one or more of pixels or voxels in the first ultrasound image data.

Optionally, the one or more processors are configured to create the second ultrasound image data by downsampling the first ultrasound image data.

Optionally, the one or more processors are configured to create the second ultrasound image data without the body being exposed to additional ultrasound pulses following acquisition of the first ultrasound image data. For example, the second ultrasound image data can be created using the exact same data that is the first ultrasound image data, or that is at least a portion of the exact same data that is the first ultrasound image data.

Optionally, the one or more processors are configured to render a three-dimensional image of the body as the multi-dimensional image.

Optionally, the one or more two-dimensional images are two-dimensional slices through the body.

Optionally, the first ultrasound image data is three-dimensional ultrasound image data.

Optionally, the first ultrasound image data is four-dimensional ultrasound image data.

In one embodiment, a method includes acquiring first ultrasound image data of a body at a first spatial resolution, generating two-dimensional image slices of the body using the ultrasound image data at the first spatial resolution, modifying the first ultrasound image data into second ultrasound image data by reducing the first spatial resolution of the first ultrasound image data to a second spatial resolution, and rendering a three-dimensional image of the body using the second ultrasound image data at the reduced, second spatial resolution.

Optionally, modifying the first ultrasound image data includes averaging values of one or more of pixels or voxels in the first ultrasound image data.

Optionally, modifying the first ultrasound image data includes downsampling the first ultrasound image data.

Optionally, the first ultrasound image data is three-dimensional ultrasound image data or four-dimensional ultrasound image data.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   acquiring first ultrasound image data of a body at a first acquisition quality level;
   displaying one or more two-dimensional images of the body using the first ultrasound image data at the first acquisition quality level;

creating second ultrasound image data at a reduced, second acquisition quality level relative to the first acquisition quality level, the second ultrasound image data created from the first ultrasound image data, wherein the first and second ultrasound image data are defined by respective three-dimensional voxels, and the voxels of the second ultrasound image data are one or more of fewer in total number or larger in size than the voxels of the first ultrasound image data; and displaying a rendered multi-dimensional image of the body using the second ultrasound image data at the reduced, second acquisition quality level.

2. The method of claim 1, wherein the first and second acquisition quality levels refer to spatial resolution such that the rendered multi-dimensional image is displayed with a reduced spatial resolution relative to the one or more two-dimensional images.

3. The method of claim 1, wherein creating the second ultrasound image data includes reducing a spatial resolution of the first ultrasound image data.

4. The method of claim 1, wherein creating the second ultrasound image data includes downsampling the first ultrasound image data.

5. The method of claim 1, wherein creating the second ultrasound image data includes applying a low-pass kernel filter to the first ultrasound image data.

6. The method of claim 1, wherein the second ultrasound image data is created without exposing the body to additional ultrasound pulses following acquisition of the first ultrasound image data.

7. The method of claim 1, wherein the rendered multi-dimensional image of the body that is displayed is a rendered three-dimensional image of the body.

8. The method of claim 1, wherein the one or more two-dimensional images represent two-dimensional slices through the body.

9. The method of claim 1, wherein the first ultrasound image data is three-dimensional ultrasound image data.

10. The method of claim 1, wherein the one or more two-dimensional images of the body and the rendered multi-dimensional image of the body are displayed on a same display device.

11. The method of claim 1, wherein the second ultrasound image data is created by averaging values of a group of multiple voxels in the first ultrasound image data to generate a voxel in the second ultrasound image data.

12. A method comprising:
acquiring first ultrasound image data of a body at a first acquisition quality level;
displaying one or more two-dimensional images of the body using the first ultrasound image data at the first acquisition quality level;
creating second ultrasound image data at a reduced, second acquisition quality level relative to the first acquisition quality level, the second ultrasound image data created from the first ultrasound image data by averaging values of a group of multiple pixels or voxels in the first ultrasound image data to generate a pixel or voxel in the second ultrasound image data; and displaying a rendered multi-dimensional image of the body using the second ultrasound image data at the reduced, second acquisition quality level.

13. A system comprising:
one or more processors configured to receive first ultrasound image data of a body that was obtained at a first acquisition quality level, the one or more processors configured to direct display of one or more two-dimensional images of the body using the first ultrasound image data at the first acquisition quality level,
wherein the one or more processors also are configured to create second ultrasound image data at a reduced, second acquisition quality level relative to the first acquisition quality level, the second ultrasound image data created from the first ultrasound image data by averaging values of a group of multiple pixels or voxels in the first ultrasound image data to generate a pixel or voxel in the second ultrasound image data,
wherein the one or more processors also are configured to direct display of a rendered multi-dimensional image of the body using the second ultrasound image data at the reduced, second acquisition quality level.

14. The system of claim 13, wherein the first acquisition quality level is a first spatial resolution of the first ultrasound image data and the second acquisition quality level is a reduced, second spatial resolution of the first ultrasound image data.

15. The system of claim 13, wherein the one or more processors are configured to create the second ultrasound image data by reducing a spatial resolution of the first ultrasound image data.

16. The system of claim 13, wherein the one or more processors are configured to create the second ultrasound image data by downsampling the first ultrasound image data.

17. A method comprising:
acquiring first ultrasound image data of a body at a first spatial resolution;
displaying one or more two-dimensional image slices of the body using the first ultrasound image data at the first spatial resolution;
modifying the first ultrasound image data into second ultrasound image data by reducing the first spatial resolution of the first ultrasound image data to a reduced, second spatial resolution, wherein the first spatial resolution is reduced to the second spatial resolution by averaging values of a group of multiple pixels or voxels in the first ultrasound image data to generate a pixel or voxel in the second ultrasound image data; and
displaying a rendered three-dimensional image of the body using the second ultrasound image data at the reduced, second spatial resolution.

18. The method of claim 17, wherein modifying the first ultrasound image data includes downsampling the first ultrasound image data.

19. The method of claim 17, wherein the first ultrasound image data is three-dimensional ultrasound image data or four-dimensional ultrasound image data.

* * * * *